United States Patent [19]
Roberts

[11] Patent Number: 5,181,529
[45] Date of Patent: Jan. 26, 1993

[54] KIT AND TWO-STEP COSMETIC TREATMENT FOR HAIR

[76] Inventor: David Roberts, 7241 Mission Hill Dr., Las Vegas, Nev. 89113

[21] Appl. No.: 732,468

[22] Filed: Jul. 18, 1991

[51] Int. Cl.$^5$ .......................... A61K 7/06; A61K 7/08
[52] U.S. Cl. ..................... 132/209; 424/47; 424/70; 424/71
[58] Field of Search ............ 132/202, 203, 209; 424/47, 70, 71

[56] References Cited

U.S. PATENT DOCUMENTS

| | | | |
|---|---|---|---|
| 3,650,280 | 3/1972 | Roberts et al. | 132/7 |
| 3,902,507 | 9/1975 | Kinney et al. | 424/71 |
| 4,668,508 | 5/1987 | Grollier et al. | 424/70 |
| 4,673,569 | 6/1987 | Shernov et al. | 424/47 |
| 4,744,978 | 5/1988 | Homan et al. | 424/70 |
| 4,761,273 | 8/1988 | Grollier et al. | 424/70 |
| 4,764,363 | 8/1988 | Bolich, Jr. | 424/47 |
| 4,770,873 | 9/1988 | Wolfram et al. | 424/71 |
| 4,834,968 | 5/1989 | Bolich, Jr. | 424/47 |
| 4,913,743 | 4/1990 | Brode et al. | 424/71 |
| 4,913,893 | 4/1990 | Varco et al. | 424/47 |
| 5,100,658 | 3/1992 | Bolich, Jr. et al. | 424/71 |

*Primary Examiner*—Gene Mancene
*Assistant Examiner*—Frank A. LaViola
*Attorney, Agent, or Firm*—Morgan & Finnegan

[57] ABSTRACT

A hair kit for beautifying and forming any hair texture is provided. The kit contains a hair treatment concentrate and a hair setting mousse. The hair treatment concentrate contains aged or unaged glyoxal, urea or thiourea, an inert carrier (e.g., water and/or a lower alkanol), and other ingredients. The hair setting mousse contains the concentrate described above, an alcohol, a foaming agent, and a propellant. With thin, fine, or curly hair, the concentrate is applied to the hair roots of the shampooed, rinsed, and towel-dried hair and then the mousse is applied to the hair shaft before the hair is groomed and dried. With thick, coarse, or damaged hair, the mousse is applied first to the shampooed, rinsed, and towel-dried hair, and the concentrate is then applied sparingly to the roots before or after grooming and drying the hair.

20 Claims, No Drawings

KIT AND TWO-STEP COSMETIC TREATMENT FOR HAIR

BACKGROUND OF THE INVENTION

This invention relates to the cosmetic treatment of hair. More particularly, it relates to a combination hair treatment and a process for beautifying hair, particularly living human hair.

It is a matter of common knowledge and experience that the hair covering of an animal, for example, the coating of hairs on a human head, varies with the individual. This variation can be characterized as ranging from coarse, thick hair down through various degrees of less thick hair ultimately to fine, thin, limp hair. Furthermore, many cosmetic treatments have been proposed to beautify and to correct defects in hair, e.g., to curl straight hair, to thicken fine hair, or to recondition hair which has been damaged by overexposure to sun, dyes, bleaches, and the like or by overprocessed permanents.

It is well known that coarse, thick hair is difficult to mold and style and, once styled, to keep in place. It has been proposed to use creams, oils, alcohols, fats such as lanolin, and styling gels as cosmetic aids to mold thick hair, but none of these are entirely satisfactory because certain of them impart a greasy look to the hair while with others often an additional hair spray coating is needed to retain the styling.

On the other hand, softer textured hair and thin hair also present problems in styling. For example, after treatment with gummy greases and oils or alcohols, softer textured fine hair appears to become thinner and less agreeable to the eye. To illustrate, four hairs may become "glued" into one. This problem is especially acute in so-called baby fine hair where the thin hairs lay very close to the head. In addition, sparse hair in men and women who have lost or begun to lose hair due to age or for other reasons must be styled to take full advantage of the natural hair available and the grooming aids discussed above, which subtract body, are entirely unacceptable.

Hair lacking elasticity also is difficult to style and manage. Hair that has been over-processed by being chemically penetrated for tinting or bleaching and the like, over and over again, usually is damaged and will no longer take a set. The hair just hangs limp and lifeless. Sets are ineffective because the elasticity has been lost. Many so-called conditioners have been proposed, but few of them elasticize the hair. They function by putting a coating on the hair and give the hair the appearance of being well-set. When you break this coating, the hair immediately returns to its limp and lifeless appearance. Nevertheless, hair treated with such conditioners lacks the desirable "spring" seen in normally elastic hair.

The desire to have hair (human or other animal) retain a particular shape or configuration is one that is widely held. Approaches taken can either involve permanent alteration of the hair or a temporary alteration. The former involves the use of chemical agents to react with the hair in order to achieve the desired effect. This process can be carried out at either room or elevated temperature.

The temporary set to hair is, as the term indicates, a temporary arrangement which can be removed by water or by shampooing. The materials used to provide the set have generally been resins or gums. The setting compositions have generally taken the form of gels, lotions, sprays, and aerosol foams (also referred to as mousses). The compositions are applied most often to hair dampened with water, spread through the hair, and let dry. The set given will vary depending on the materials used.

It has been found that thick, thin, and damaged hair can be beautified in a surprisingly efficient manner by treating the hair with a non-alkaline cosmetic composition according to the teachings of U.S. Pat. No. 3,650,280 (issued Mar. 21, 1972 to David Roberts). While the compositions of the '280 patent beautify the hair, they do not shorten the time required to achieve the desired look nor do they improve the hold.

It is therefore an object of the present invention to provide a hair treatment combination that beautifies the hair, shortens the time required to achieve the desired look, and improves the hold.

SUMMARY OF THE INVENTION

The present invention provides a hair treatment kit for use in a combined hair treatment regime. The kit comprises a combination of (a) a hair setting mousse and (b) a hair treatment concentrate. This all purpose kit contains all one needs for any type of hair texture or condition of the hair shaft. The kit can be used by all members of the family no matter what their hair texture or condition, with each person determining the combination that is best for them and adjusting the application to meet their hair's requirements. The use of this kit can make everyone a professional.

The hair setting mousse comprises (i) an effective amount of a hair treatment concentrate (described hereafter), e.g., from about 70 to 90%, preferably about 75 to 85%, most preferably about 84%; (ii) an effective amount of a propellant, e.g., about 5 to 15%, preferably about 7.5 to 12.5%, most preferably about 10%; (iii) an effective amount of a foaming agent, preferably about 0.5 to 5%, and (iv) optionally an effective amount of an alcohol, e.g., 0 to about 10%, the percentages being by weight and totalling 100%. Typically, the combination of the foaming agent and the alcohol is about 10 to 12%, preferably 11%.

The use of this particular hair treatment concentrate in the mousse has been found to be essential. As will be shown hereafter, if mousse without the hair treatment concentrate or with a different concentrate is used, the desired effect is not achieved.

Suitable hair treatment concentrates are described in U.S. Pat. No. 3,650,280, cited above, the disclosure of which is incorporated herein by reference. The concentrate comprises (i) from about 0.08 to about 9 wt. %, preferably about 5 to 6 wt. %, of aged or unaged glyoxal, (ii) about 0.2 to about 9 wt. %, preferably about 5 to 6 wt. %, of urea or thiourea, and (iii), as an inert carrier, water, a lower alkanol, or mixtures thereof.

The process of the present invention is carried out by applying both the hair treatment concentrate and the hair setting mousse to the hair. Even though two treatments are involved, they are simple to carry out and quickly accomplished.

With thin hair, fine hair, or curly hair the process is carried out by (a) shampooing, rinsing, and towel-drying the hair; (b) applying the hair treatment concentrate to the roots of the towel-dried hair in an amount sufficient to impart the desired degree of thickening, lifting, and/or molding, which will depend upon the hair type and the hold desired; (c) then applying the hair setting mousse to the hair shaft in an amount sufficient to aid in grooming the hair into the desired shape; and (d) grooming the treated and moussed hair into the desired shape; and (e) drying the shaped hair during or after grooming. The hair concentrate is applied to the roots first and then immediately the hair setting mousse is applied to the hair shaft. A small amount of the concentrate is put on the fingertips, worked into the hair roots at the scalp, and this procedure is repeated three or four times. With curly hair typically one would use more of the concentrate and less of the mousse. With thin or fine hair one would use less of the concentrate and more of the mousse.

With coarse hair or damaged hair (i e., over-processed hair) the process is carried out by (a) shampooing, rinsing, and towel-drying the hair; (b) applying the hair setting mousse to the towel-dried hair in an amount sufficient to aid in moist grooming the hair into the desired shape; (c) applying, before or after grooming and drying, the hair treatment concentrate to the hair in an amount sufficient to act as a sealant for the groomed hair, which will depend upon the hair type and the hold desired; (d) grooming the moussed and optionally treated hair into the desired shape; and (e) drying the shaped hair during or after grooming. The hair setting mousse is applied first and the hair care concentrate is applied sparingly to the hair roots after application of the mousse and before or after grooming and drying. Using the mousse first gives the coarse hair flexibility and the damaged hair elasticity. Typically one uses the mousse liberally and applies the concentrate sparingly.

Grooming can be done by allowing the hair to dry naturally or by blow drying, setting, or other conventional means known to those skilled in the art.

The combination treatment beautifies the hair, shortens the time required to achieve the desired look, and maximizes the hold. The combination hair treatment is effective for all hair types. Fine or thin hair is given volume by thickening the hair shaft and microscopically lifting the hair from the scalp so it appears thicker. Curly hair is given the strength needed to temporarily retain the molded and straighter shape. Coarse hair is softened so it has the ability to retain the groomed shape. Damaged hair is elasticized so that it is flexible and able to hold the groomed shape.

DESCRIPTION OF THE PREFERRED EMBODIMENTS

As used herein, the term "non-alkaline" contemplates compositions in which the pH is from neutral to acidic, i.e., about pH 7 or below. Excluded, of course, are media too acidic to be employed on the hair or skin without imparting damage. In any event, alkaline media, i.e., those of above pH 7 are excluded, and especially those alkaline pH's commonly encountered in hair waving compositions (wherein the optimum pH seems to be about pH 9.2). In the present non-alkaline hair treatment concentrates, the preferred pH for most purposes is from about 4 to about 6.

"Thickening" thin hair means changing the hair in such a way that the hair appears heavier and fuller. The hair is lifted from the scalp and simultaneously given body. "Lifting" makes the hair look thicker. "Body" makes the hair feel thicker. Hair can be bodified (i.e., feel thicker) but will not look thicker if the hair remains flat to the head and is not lifted off the scalp.

"Molding" thick hair is a term well understood by hair stylists. It means treating the hair to cause it to conform to a generally predetermined, but more desirable, configuration than the unmolded hair assumes.

"Elasticizing" hair means causing a change in the hair so that the hair will easily take a set and afterwards feel and look "springy".

"Grooming" means the usual and customary operations employed to arrange hair such as combing, recombing, brushing, blow drying, setting, and the like. "Setting" contemplates all the operations commonly employed to style hair and includes curling, waving, arranging, and the like.

The urea (or thiourea) and glyoxal ingredients used in the present hair treatment concentrate are items of commerce. They have been found to be essential. It is not possible to use either urea (or thiourea) or glyoxal alone and obtain the desired results. Only a marginal effect will be seen with each used alone. However, a remarkable penetrating, swelling and surrounding of the outer structure of the hair is seen if the hair is treated with urea and glyoxal used together under non-alkaline conditions in an inert cosmetic carrier. While thiourea can be used in place of urea and give good results, urea is preferred because it is not toxic.

Aged as well as non-aged glyoxal can be used. Aged glyoxal may be obtained by allowing the glyoxal to remain in the drum for at least four months before using it. The advantages provided by the use of the aged glyoxal are that the pH and specific gravity are reduced.

The carriers used in the present hair treatment concentrate comprise a class of non-irritating liquids which may be safely applied to the skin and hair of mammals. Suitable carriers include water, alcohols, especially $C_2$–$C_6$ alcohols such as ethanol and isopropanol, mixtures of water and lower alcohols, fats such as lanolin, and the like.

The ratio of the amount of urea (or thiourea) and glyoxal to the amount of carrier used is not particularly critical. Suitable formulations, depending on the end use contemplated, can be prepared easily by those skilled in the art. Generally, for economic reasons and for ease of application, the hair treatment concentrate will contain a minor proportion of urea and glyoxal and a major proportion of the carrier. For most purposes, the ratio of glyoxal to urea will not be critical, the advantages being secured at ratios ranging from about 1:10 to about 10:1 by weight of each. For thickening thin hair, molding thick hair, and for elasticizing damaged hair, however, generally preferred ratios will comprise for each part by weight of glyoxal, from about 1 to about 10 parts by weight of urea, preferably from about 2.5 to about 3.5 parts by weight of urea. For most purposes, the best properties will be obtained with concentrates containing from about 0.04 to about 9% glyoxal, preferably from about 0.08 to about 4% by weight, and from about 0.1% to about the solubility limit in water of urea, preferably from about 0.20 to about 9%.

If either benzyl alcohol, diethylene glycol monoethyl ether, or both is added to the hair treatment concentrate in minor proportions (e.g., either or both together providing less than 50% by weight of the final composition), there is a preferred enhancement in the properties of the concentrate. Concentrates containing either of these ingredients or, preferably both of them, are important embodiments of the '280 patent. While the reasons for their contributions to enhanced properties are not clearly understood, the use of benzyl alcohol and diethylene glycol monoethyl ether in minor proportions, e.g., especially from about 0.1 to about 4% by weight and preferably from about 0.1 to about 2% by weight of each, facilitates penetration and reduces the time required to obtain the desired results.

Hair treatment concentrates having a pH of 4–6 and the following composition, expressed as parts by weight, are preferred:

| | |
|---|---|
| glyoxal | 0.33–1.2 |
| urea | 1–4 |
| hydrolyzed protein (Wilson, X-1000) | 0.25 |
| polyvinylpyrrolidone (PVP NPK 30) | 0.05 |
| diethyleneglycol mono ethyl ether (Union Carbide, Carbitol) | 1–2 |
| benzyl alcohol | 1–2 |
| carboxypolymethylene (Union Carbide, Carbopoly 940) | 0.8–1.0 |
| sodium hydroxide | 0.15–0.2 |
| formalin | 0.25 |
| perfume | q.s. |
| opacifier | q.s. |
| water q.s. | 100.00 |

A preferred mousse comprises (a) from about 78% to about 90% of the preferred hair treatment concentrate described above; (b) about 4 to about 15% of isobutane and propane as the propellant; (c) about 0.5 to about 5% of tallow trimonium chloride as the foaming agent; and (d) 0 to about 10% of a denatured alcohol.

The agent responsible for expelling the other materials from the container and forming the mousse character is a propellant. The propellant used in the mousse is conventional. Any liquefiable gas conventionally used for aerosols can be used. Preferably, the density of the propellant or mixture thereof is less than 1 so that pure propellant is not emitted from the container. Examples of suitable materials include hydrocarbons such as propane, n-butane, isobutane, trichlorofluoromethane, dichlorodifluoromethane, dichlorotetrafluoroethane, monochlorodifluoromethane, trichlorotrifluoroethane, and the like used singly or in admixture. Isobutane and admixtures thereof with other hydrocarbons are preferred due to the fact that their densities are less than 1. Especially preferred propellants are combinations of isobutane and propane, such as those identified as A46 or A70 which are available from Aerosol Services.

The amount of the propellant used is governed by normal factors well known in the aerosol art. The level of propellant is generally from about 5% to about 20%, preferably from about 7% to about 15% of the total mousse composition.

The foaming agent used in the mousse is conventional and may be selected from the group consisting of nonionic or cationic foaming agents. Especially preferred foaming agents are quaternary ammonium compounds such as tallow trimonium chloride (sold under the trade name Oleth-20 and available from Croda or D&D Chemicals.

The alcohol used in the mousse is conventional and may be selected from the group consisting of ethyl or isopropyl alcohol. An especially preferred alcohol is denatured ethyl alcohol.

Of course, as will be obvious to those skilled in the art, a variety of conventional additives may be used in the hair treatment concentrates to secure additional objectives. For example, small amounts of stabilizers and sequestrants (e.g., sorbic acid or its salts; gelling agents such as polyethers; opacifiers; hydrolyzed proteins; perfumes and the like) may be used in the concentrate. Also, pigments, antiseptics and like can be added to the concentrate. These additives will comprise generally a minor proportion of the concentrate, e.g., up to about 2% by weight in the preferred concentrates.

The aerosol mousses herein also can contain a variety of nonessential, optional components suitable for rendering such compositions more acceptable. Such conventional optional ingredients include emulsifiers such as anionics (e.g., sodium alkyl sulfate) and nonionics (amine oxides); preservatives such as benzyl alcohol, ethyl paraben, propyl paraben and imidazolidinyl urea; cationic emulsifiers/conditioners such as cetyl trimethyl ammonium chloride, stearyldimethyl benzyl ammonium chloride, and di (partially hydrogenated tallow) dimethylammonium chloride; thickeners and viscosity modifiers such as a diethanolamide of a long chain fatty acid; block polymers of ethylene oxide and propylene oxide such as Pluronic F88 offered by BASF Wyandotte, fatty alcohols such as cetearyl alcohol, sodium chloride, sodium sulfate, and ethyl alcohol, and perfume oils. These optional materials are generally used individually at a level of from about 0.01% to about 10%, preferably from about 0.5% to about 5% by weight of the total composition.

There is nothing critical about the manner in which the present hair treatment concentrates and hair setting mousses are prepared. Those skilled in the art of formulating cosmetics will be well aware of the manipulative techniques needed to provide the mousse in the form of foams and the concentrates in the form of solutions, dispersions, lotions, gels, creams and the like.

Methods of preparing mousses are described in U.S. Pat. No. 4,913,893 (issued Apr. 3, 1990 to J. J. Varco et al.), U.S. Pat. No. 4,834,968 (issued May 30, 1989 to R. E. Bolich, Jr.), U.S. Pat. No. 4,764,363 (issued Aug. 16, 1988 to R. E. Bolich, Jr.), U.S. Pat. No. 4,744,978 (issued May 17, 1988 to G. R. Homan et al.), and U S. Pat. No. 4,673,569 (issued Jun. 16, 1987 to S. L. Shernov et al.), the disclosures of which are incorporated herein by reference. The method of preparing the hair setting mousses of the present invention follows conventional aerosol filling procedures. In one method, the concentrate, in an appropriate amount, is placed in an aerosol container. The container is then fitted with a valve, subjected to a vacuum to rid the container of air and sealed with the valve "crimped" in place. The propellant is introduced into the container through the valve.

The present hair setting mousses and hair treatment concentrates can be applied to the hair by any method satisfactory to accomplish the desired beautification, grooming, and holding. For best results, the hair will be shampooed, then rinsed clean and towel-dried.

The concentrate is applied like any hair dressing in varying amounts, with the amount used depending on the hair type or texture. With thin or fine hair where the concentrate is applied first, more concentrate is used and the concentrate is applied more liberally and worked into the scalp and hair roots with the fingers. Three or four applications using small amounts of the concentrate are preferred. With thick or overprocessed hair where the concentrate is applied last, much less concentrate is used and it is applied sparingly to the hair shaft. The mousse, emitted from the aerosol container as a foam, is applied liberally to the hair shaft and distributed evenly through the hair with the fingers or with a hair styling implement. With thin, fine, or curly hair the mousse is applied after the concentrate. With thick or overprocessed hair the mousse is applied first.

The hair is then groomed and dried either naturally or blow dried. The mousse and/or concentrate at this point appear to have penetrated the hair structure and to have adhered to the outer surface of the hair to produce thickening, molding, and/or elasticizing.

Whenever additional body is desired, a re-application of the hair treatment concentrate on the already groomed hair will secure the desired results.

The advantages of the combined treatment are:

(1) the beautifying advantages reported in the '280 patent (i.e., thickening of thin hair, molding of thick hair, and elasticizing of damaged hair) are enhanced and the beautifying effect lasts longer (e.g., up to the time of the next shampoo);

(2) the desired end look is achieved in less time (e.g., 5 minutes instead of 30 minutes); and (3) the hair holds the imparted shape better and for a longer time because the natural hair oils do not weaken the body achieved.

All hair becomes softer after shampooing and is depleted of vitality and strength. This happens regardless of the shampoo type used. The present combined treatment with the hair treatment concentrate and hair setting mousse replaces, upon application, the lost strength and elasticity and gives the hair a thicker feeling, particularly fine hair. While the mousse gives flexibility and shape, with fine, thin, or curly hair it is necessary to use the hair treatment concentrate to coarsen the texture. In addition, using the mousse together with the concentrate gives a firmer shape to all hair types.

Thus, the two-step treatment is better than either treatment alone. Use of the hair setting mousse alone is not completely satisfactory, particularly for fine, thin, or curly hair.

The following Examples further describe and demonstrate preferred embodiments within the scope of the present invention and show that use of the present hair setting mousse with another hair treatment concentrate or present concentrate with another mousse does not provide the desired effect. This is believed to be due to incompatibility of the different compositions. The compatibility between the present mousse and present concentrate is good. The examples are given solely for the purpose of illustration and are not to be construed as limitations of the present invention as many variations thereof are possible without departing from its spirit and scope.

EXAMPLE 1

A hair treatment concentrate having the following formulation, expressed as parts by weight, was prepared:

| | |
|---|---|
| glyoxal | 1.4 |
| urea | 4 |
| water | 94.6 |

The urea was mixed with the water until dissolved. Then glyoxal was added as a 40 percent aqueous solution. Finally, the mixture was blended until uniform and the pH was adjusted to 4 to 6, if necessary, with acid or alkali (e.g., with 0.1 N hydrochloric acid or 0.5 N sodium hydroxide).

EXAMPLE 2

Hair treatment concentrates having the following formulations, expressed as parts by weight, were prepared:

| | | | | | | |
|---|---|---|---|---|---|---|
| glyoxal | 1.4 | 1.4 | 1.4 | 1.4 | 1.2 | 1.6 |
| urea | 4 | 4 | 4 | 4 | 4 | 4 |
| benzyl alcohol | — | 2 | — | 2 | 2 | 2 |
| diethylene glycol monoethyl ether | — | 92.6 | 92.6 | 90.6 | 90.8 | 90.4 |
| isopropanol | 94.6 | — | — | — | — | — |

The pH was adjusted to 4 to 6, if necessary by adding 0.1 N hydrochloric acid or 0.5 N sodium hydroxide.

EXAMPLE 3

A hair treatment concentrate having the following formulation, expressed as parts by weight, was prepared:

| | |
|---|---|
| glyoxal | 0.4 |
| urea | 2.0 |
| hydrolyzed protein (Wilson, X-1000) | 0.1 |
| carboxypolymethylene (Union Carbide Carbopol 940) | 1.0 |
| diethyleneglycol monoethyl ether (Union Carbide, Carbitol) | 2.0 |
| benzyl alcohol | 2.0 |
| potassium sorbate | 0.05 |
| perfume | q.s. |
| sodium hydroxide | 0.175 |
| opacifier | q.s. |

EXAMPLE 4

A hair treatment concentrate having the formulation of Example 3 was prepared except that 5 parts each of glyoxal and urea were used and the quantity of water added was adjusted accordingly.

EXAMPLE 5

Hair treatment concentrates having the formulations described in Examples 2, 3, and 4 were modified by using aged glyoxal instead of unaged glyoxal. The aged glyoxal was glyoxal which had been stored in the drum for about one year.

EXAMPLE 6

A hair setting mousse having the following formulation, expressed as parts by weight, was prepared:

| | |
|---|---|
| concentrate of Example 3 | 84% |
| alcohol and foaming agent | 11% |
| propellant | 5% |

EXAMPLE 7

This example describes the application of the hair treatment concentrate of Example 4 to thin hair which was fine and sparse, followed by immediate application of the hair setting mousse of Example 6.

The concentrate was applied to the roots of the shampooed, rinsed, and towel-dried hair. An amount (e.g., corresponding to the amount of toothpaste applied as a strip to a toothbrush) is placed on the fingertips of one hand, spread onto the fingertips of the other hand, and then worked into the scalp. The application was repeated four times. The mousse was then applied to the hair. The amount of mousse applied was about the size of a tennis ball. The hair was groomed by blow drying.

The hair showed an improved degree of firmness, i.e., when finger-combed or combed it had a coarser feeling and was lifted up from the scalp. It was easier to groom and style into the desired shape.

EXAMPLE 8

This example describes the application of the hair setting mousse of Example 6 to thin hair which was fine and sparse, followed immediately by application of the hair treatment concentrate of Example 4.

The mousse was applied to the shampooed and towel-dried hair using the amount described in Example 6. The concentrate was then applied using the amount described in Example 6. The hair was blow dried.

The results showed that the fine hair had considerably more body, that the formerly "feather-like" hair felt stronger and firmer to the touch, and that there was a slight lifting of the hair off the scalp at the base of the hair. However, the lift achieved in Example 6 was better and gave the hair a fuller appearance.

EXAMPLE 9

This example describes the application of the hair setting mousse of Example 6 to thick hair which is wirey, shapeless, and without form, followed by application of the hair treatment concentrate of Example 4 to the dry shaped hair.

The mousse and concentrate are applied as in Example 8 and the hair is groomed by blow drying.

The wirey stiff feeling of the hair should be softened so that styling will be easy and the hair will hold the groomed appearance.

EXAMPLE 10

This example describes the application of the hair treatment concentrate of Example 4 to hair which was over-processed and damaged from coloring and permanents, followed by the immediate application of the hair setting mousse of Example 6.

After the concentrate is applied using the procedure described in Example 8, the mousse is applied to the hair shaft.

The wirey stiff feeling of the hair should be softened so that styling will be easy. The hair should hold the shape and mold the head.

EXAMPLE 11

This example describes the application of the hair setting mousse of Example 6 to hair which was over-processed and damaged from coloring and permanents, followed by the application of the hair treatment concentrate of Example 4 to the dry shaped hair.

After the mousse is applied using the procedure described in Example 7, it should require only a small amount of the concentrate to achieve the desired results. Styling should be easier. When the hair is dried and recombed, the hair should have body and elasticity and the styling should last until the hair is washed again.

EXAMPLE 12 (COMPARATIVE)

Part A

Using the procedure of Example 7, Clairol Styling Mousse (maximum control) was applied to fine hair, followed by Clairol Conditioner Styling Gel (extra hold) using the amounts recommended.

Part B

Using the above procedure Gellee mousse was applied to fine hair, followed by Gellee concentrate using the amounts recommended.

Neither combination gave acceptable results. The main disadvantage of the above products was that the hair lacked elasticity. The Gellee products gave poorer results than the Clairol products.

EXAMPLE 13 (COMPARATIVE)

Using the procedure of Example 7, an additional test was carried out on fine hair. Clairol Styling Mousse (maximum control) was used first, followed by the hair treatment concentrate of Example 4.

The results were not as good as those obtained by applying the hair setting mousse of Example 5, followed by the hair treatment concentrate of Example 3. The hair did not have the same body nor did it retain what body it had over time. In contrast, hair treated with the hair setting mousse of Example 6 and hair treatment concentrate of Example 4 was more full bodied (i.e., fuller with added firmness and/or easier control), the concentrate was quicker acting in sealing the shape, and time enhanced its effectiveness, rather than reducing its effectiveness (which is the opposite of what one would expect). This is the opposite of what one would expect since most products become less effective after time passes due to body heat and/or hair oils.

EXAMPLE 14 (COMPARATIVE)

Using the procedure of Example 6, an additional test was carried out on fine hair using the hair setting mousse of Example 5 followed by the Clairol Conditioner Styling Gel described in Example 11.

The results were not as good as those obtained by applying the hair setting mousse of Example 6 followed by the hair treatment concentrate of Example 4. The hair had body but was flatter (i.e., the hair was not lifted off the scalp and did not puff up). Also, the hair could not be as rapidly shaped on blowing out. The use of the present concentrate provides the additional volume that this particular hair type required.

Now that the preferred embodiments of the invention have been described in detail, various modifications and improvements thereon will become readily apparent to those skilled in the art. Accordingly, the spirit and scope of the present invention are to be limited only by the appended claims and not by the foregoing specification.

What is claimed is:

1. A hair care kit which comprises a combination of:
   (a) hair setting mousse and
   (b) a hair treatment concentrate; wherein the mousse of (a) comprises:
   (i) an effective amount of a hair treatment concentrate which comprises about 0.08 to about 9% by weight of aged or unaged glyoxal, about 0.2 to about 9% by weight of urea or thiourea, and, as an inert carrier, water, a lower alkanol, or mixtures thereof;
   (ii) an effective amount of a propellant;
   (iii) an effective amount of a foaming agent; and
   (iv) an effective amount of an alcohol: and wherein the hair treatment concentrate of (b) comprises:

(i) about 0.08 to about 4% by weight of aged or unaged glyoxal;
(ii) about 0.2 to about 9% by weight of urea or thiourea; and
(iii) as an inert carrier, water, a lower alkanol, or mixtures thereof.

2. The hair care kit of claim 1, wherein the hair treatment concentrate further comprises about 0.1% hydrolyzed protein, about 1% carboxypolymethylene, about 0.1 to about 4% of diethylene glycol monoethyl ether, about 2% benzyl alcohol, about 0.05% potassium sorbate, and about 0.175% sodium hydroxide.

3. The hair care kit of claim 2, wherein the hair treatment concentrate comprises about 5–6% glyoxal, about 5–6% urea, and about 2% diethyleneglycol monoethyl ether.

4. The hair care kit of claim 3, wherein the hair treatment concentrate comprises aged glyoxal.

5. The hair care kit of claim 3, wherein the pH of the hair treatment concentrate is from about 4 to 6.

6. The hair care kit of claim 1, wherein in the mousse of (a) the hair care concentrate is present in an amount of about 70–90% by weight; wherein the alcohol is present in an amount of about 0–10% by weight and is a denatured alcohol; wherein the foaming agent is present in an amount of about 0.5 to 5% by weight and is tallow trimonium chloride and wherein the propellant is present in an amount of about 5 to 15% by weight and is selected from the group consisting of isobutane, propane, and mixtures thereof.

7. The hair care kit of claim 2, wherein in the mousse of (a) the hair care concentrate is present in an amount of about 75 to 85% by weight; wherein the foaming agent is present in an amount of about 0.5 to 5% by weight and is tallow trimonium chloride; and wherein the propellant is present in an amount of about 7.5 to 12.5% by weight and is selected from the group consisting of isobutane, propane, and mixtures thereof.

8. The hair care kit of claim 3, wherein in the mousse of (a) the hair care concentrate is present in an amount of about 84% by weight; wherein the propellant is present in an amount of about 5% by weight and is selected from the group consisting of isobutane, propane, and mixtures thereof; wherein the foaming agent and the alcohol are present in a amount of about 11% by weight and wherein the foaming agent is tallow trimonium chloride and the alcohol is a denatured alcohol.

9. The hair care kit of claim 8, wherein the denatured alcohol present in the mousse is a lower alcohol and wherein the inert carrier in the hair treatment concentrate is water, a denatured lower alcohol, or mixtures thereof.

10. A process for beautifying and grooming hair which comprises separately applying to the hair a hair treatment concentrate and a hair setting mousse; the hair treatment concentrate comprising (i) about 0.08 to about 9% by weight of aged or unaged glyoxal, (ii) about 0.2 to about 9% by weight of urea or thiourea, and (iii), as an inert carrier, water, a lower alkanol, or a mixture thereof; the hair setting mousse comprising (i) an effective amount of the hair treatment concentrate, (ii) an effective amount of a propellant, (iii) an effective amount of an alcohol, and (iv) an effective amount of a foaming agent.

11. The process of claim 10 for beautifying and grooming thin, fine, or curly hair, which comprises the steps of:
(a) shampooing, rinsing and towel-drying the hair;
(b) applying the hair treatment concentrate to the roots of the towel-dried hair in an amount sufficient to provide lift and body to the hair;
(c) then applying the hair setting mousse to the hair shaft in an amount sufficient to provide volume and aid in grooming the hair into the desired shape;
(d) grooming the treated and moussed hair into the desired shape: and
(e) drying the shaped hair during or after grooming.

12. The process of claim 10 for beautifying and grooming thick or damaged hair which comprises the steps of:
(a) shampooing, rinsing and towel-drying the hair;
(b) applying the hair setting mousse to the towel-dried hair in an amount sufficient to provide flexibility and elasticity to the hair;
(c) grooming the hair into the desired shape;
(d) drying the shaped hair during or after grooming; and
(e) applying the hair treatment concentrate to the hair after step (b) or step (d) in an amount sufficient to improve the hold.

13. The process of claim 10, wherein the hair treatment concentrate further comprises about 0.1% hydrolyzed protein, about 1% carboxypolymethylene, about 0.1 to about 4% of diethylene glycol monoethyl ether, about 2% benzyl alcohol, about 0.05% potassium sorbate, and about 0.175% sodium hydroxide.

14. The process of claim 13, wherein the hair treatment concentrate comprises about 5–6% glyoxal, about 5–6% urea, and about 2% diethyleneglycol monoethyl ether.

15. The process of claim 10, wherein the grooming is carried out by natural drying or blow drying, setting, or brushing.

16. The process of claim 10, wherein the grooming and drying are carried out by air-drying the hair and finger combing or brushing the hair during the air-drying.

17. The process of claim 11, which comprises the further step of applying to the dry formed hair, at some time after the grooming and drying, an additional amount of the hair treatment concentrate in an amount sufficient to improve the body.

18. The process of claim 12, which comprises the further step of applying to the dry formed hair, at some time after the first application of the hair treatment concentrate and the grooming and drying, an additional amount of the hair treatment concentrate in an amount sufficient to improve the body.

19. The process of claim 11, whereby the hair is more quickly groomed into the desired shape and held in the desired shape for about 3 to 6 days, whereby thin or fine hair is thickened and lifted off the scalp and curly hair is strengthened and temporarily molded into a straighter shape.

20. The process of claim 12, whereby the hair is more quickly groomed into the desired shape and held in the desired shape for about 3 to 6 days, whereby thick hair is softened and overprocessed hair is elasticized.

* * * * *

UNITED STATES PATENT AND TRADEMARK OFFICE
CERTIFICATE OF CORRECTION

PATENT NO. : 5,181,529
DATED : January 26, 1993
INVENTOR(S) : DAVID ROBERTS

It is certified that error appears in the above-identified patent and that said Letters Patent is hereby corrected as shown below:

Column 8, line 34, (EXAMPLE 3), after the line "opacifier    q.s."
the following additional line --water    q.s.    100.00--.

Signed and Sealed this

Eleventh Day of January, 1994

Attest:

BRUCE LEHMAN

Attesting Officer    Commissioner of Patents and Trademarks